United States Patent [19]

Nedreski

[11] 4,435,091
[45] Mar. 6, 1984

[54] DEW POINT SENSOR

[76] Inventor: Robert J. Nedreski, 5073 Wiltsie Rd., Erie, Pa. 16510

[21] Appl. No.: 286,656

[22] Filed: Jul. 24, 1981

[51] Int. Cl.$^3$ .................................... G01N 25/12
[52] U.S. Cl. ............................. 374/20; 73/336.5; 73/29
[58] Field of Search .............. 374/20; 307/311; 357/19; 250/577; 73/336.5, 29

[56] References Cited

U.S. PATENT DOCUMENTS

| | | | |
|---|---|---|---|
| 3,528,278 | 9/1970 | Sterling | 73/336.5 |
| 4,035,644 | 7/1977 | Ciemochowski | 374/20 |
| 4,082,959 | 4/1978 | Nakashima | 73/293 |
| 4,212,023 | 7/1980 | Chu | 357/19 |
| 4,216,486 | 8/1980 | Geddes | 357/19 |
| 4,286,464 | 9/1981 | Tauber | 73/293 |

*Primary Examiner*—Charles E. Frankfort
*Assistant Examiner*—Denis E. Corr
*Attorney, Agent, or Firm*—Charles L. Lovercheck; Wayne L. Lovercheck; Dale R. Lovercheck

[57] ABSTRACT

An integrated circuit device is disclosed for sensing dew point which uses integrated circuit techniques supported on a suitable substrate. Four semi-conductor junctions are used which are a Peltier junction or a junction capable of emitting or absorbing heat, a light-emitting junction, a junction that generates electrical current when exposed to light and a temperature sensing junction. The circuit cooperates to control time and switch the current through the Peltier junction to heat and cool it. The light-emitting junction emits light onto the reflecting surface. The light sensing means senses the reflected light, and the Peltier junction selectively heats and cools the reflecting surface causing moisture to condense on the surface which changes the reflecting properties of the surface and changes the amount of light to the light sensing junction. Current through the Peltier junction is then switched causing the Peltier junction to heat the reflecting surface evaporating the moisture. The Peltier junction is then reversed to start another cycle.

6 Claims, 4 Drawing Figures

DEW POINT SENSOR

GENERAL DESCRIPTION OF THE INVENTION

This invention consists of an integrated device, made by integrated circuit techniques, which detects the dew point of air or other gas containing water vapor or other condensible vapor.

The integrated device consists of four semi-conductor junctions, resistive elements and such other elements as may be needed for proper functioning, all formed by integrated circuit techniques on a suitable substrate. The substrate may be, but is not confined to, single crystal silicon. Four of the semi-conductor junctions, herein referred to as the primary junctions, are:

1. A junction exhibiting the Peltier effect—that is, emitting or absorbing heat when the electrical current is passed through the junction in an appropriate direction—which will hereafter be called the Peltier junction.

2. A junction responding to temperature changes in a reasonably linear manner, hereby known as the temperature junction. Two well-known forms of such a junction are: (a) A forward-biased diode, where the forward voltage drop is a function of temperature and (b) a bipolar transistor, where the base to emitter voltage at a given temperature is a very linear measure of temperature.

3. A junction having the property of emitting light, either in the visible region or, preferably, in the infrared region, which may be of the type known as a light-emitting diode, or of the type known as a laser diode. This junction will hereafter be called the *LED junction*.

4. A junction having the property of either generating an electrical current when exposed to light, or of allowing more electrical current to pass through it when exposed to light. This junction will be called the *sensing junction*.

The four primary junctions, together with such other junctions and other circuit elements as are needed to control, time and switch the current through the Peltier junction, measure the voltage across—or the current through—the temperature junction, maintain current through the LED junction to give constant light output and sense any change in the output of the sensing junction. All these junctions and other elements are fabricated as a monolithic, integrated device by means of standard, well-known, integrated circuit techniques. The complete structure is covered by a thick layer of silicon dioxide 11 (in the case of a silicon-based structure) or other material derived from the substrate, or deposited thereon, and having the characteristics of (a) being relatively transparent to the radiation emitted by the LED junction (b) having a refractive index significantly different than either the gas whose dew point is to be measured, or the condensed vapor, but not necessarily different than both and, (c) being a reasonably good electrical insulator. This layer will hereafter be called the insulating layer.

The four primary junctions are fabricated in such positions in the monolithic structure 10 that: (1) The temperature junction gives a highly accurate indication of the outer surface temperature of the insulation layer and (2) The light emitted from the LED junction and reflected from the outer surface of the insulating layer is received to a significant degree by the sensing junction.

METHOD OF OPERATION

1. Assuming that initially the outer surface of the insulating layer (which is exposed to the gas whose dew point it is desired to measure) is at a temperature significantly above the dew point.

2. An electrical current is caused to flow through the Peltier junction in such direction as to absorb heat and lower the temperature of the insulating layer. (Ideally, the current should be set at a value such as to cause cooling at a rate which will maintain a very small difference between the temperature at the outer surface of the insulating layer and the temperature junction.) Since the entire device is very small, temperature differences of a small fraction of a degree can be readily attained at quite rapid rates of cooling, thus permitting rapid measurements.

When the vapor condenses on the outer surface of the insulating layer, an abrupt change of reflection of light at said outer surface will occur. The type of change-increase or decrease-will depend on the relative indices of refraction of the gas, the condensed vapor and the insulating layer. In some applications, the change in reflection of light might be enhanced by lightly etching the outer surface of the insulating layer, thus causing a change from a diffuse surface to a smooth surface when the vapor condenses. This might be especially useful when the indices of refraction of the condensed vapor and the insulating layer are very similar. In a case where indices of refraction cannot be made to match suitably, surface coatings similar to those used to reduce reflections at the surface of photographic lenses could be used.

3. The change in reflection at the outer surface of the insulating layer when the vapor condenses will cause a change in the light from the LED junction falling on the sensing junction, thus giving rise to an electrical signal from the sensing junction. This signal is used to switch the output of the temperature junction to the output circuit, thus giving a measure of the dew point.

4. After a suitable time, which may be a small fraction of a second, considering the speed at which solid-state circuits operate, the current through the Peltier junction is reversed, causing the temperature of the insulating layer to increase. The result is to evaporate the vapor condensed on the outer surface. Since the condensed layer is very thin, this will occur quickly. Evaporation of the condensed vapor is indicated by a reverse change of the reflectance of light from the outer surface of the insulating layer, which in turn causes a change in the output of the sensing junction. This, in turn, again reverses the flow of current through the Peltier junction, which starts a new cycle of measurement.

REFERENCE TO PRIOR ART

The following prior art patents are known to applicant: U.S. Pat. Nos. 3,458,845; 3,516,282; 3,523,244; 3,557,619; 3,599,862; 3,630,084; 3,696,360.

The above U.S. Patents all involve the use of hygroscopic materials, such as lithium chloride, aluminum oxide or various organic compounds, as the sensing element. The function depends on the penetration of water through a relatively thick layer of the sensing element, while my invention depends on the condensation of water from the vapor state on a surface.

In all except one of the above patents (U.S. Pat. No. 3,557,619) some electrical property of the sensing element, such as resistance or impedance, is modified by the moisture in the gas and is sensed by the passage of an electrical current through the sensing element, thus exposing electrically energized parts to the gas whose water vapor content is to be measured, whereas my invention, in the preferred form, has all current-carrying parts insulated from the said gas. Even in the non-preferred form, the actual dew point measuring circuits or elements are insulated from the gas, since the exposed electrical elements act only as an "off-on" device to indicate attainment of dew point.

While all of the above devices may be described loosely as "solid-state" devices in the sense of having no gaseous or vacuum-enclosed elements, none of them approaches remotely the definition of an integrated *device*. The invention herein disclosed not only incorporates integrated circuits as a part of its structure, but uses integrated circuit technology to produce a complete *device*, including input and output elements.

All of the referenced patents involved elements external to the sensing element to make a complete humidity—or dew point-sensing device, whereas the device disclosed herein is completely self-contained, or in other words, is *an integrated device,* as described earlier, except for the power supply and read-out means.

As for U.S. Pat. No. 3,557,619, while it depends on optical, rather than electrical sensing of the measured quantity, and *thus is similar to the preferred form of my invention in avoiding* flow of electrical current in the exposed sensing element, it still—like the other patents—: (A) makes use of an *hygroscopic substance* as the sensing element; (B) is neither an integrated circuit nor an integrated device; (C) is fabricated by essentially manual methods, rather than integrated circuit techniques with their lower cost and higher precision and (D) makes use of separate, discrete, auxiliary detecting means.

OBJECTS OF THE INVENTION

It is the object of the invention to provide an improved dew point sensing device.

Another object of the invention is to provide a dew point sensing device made up of semi-conductor junctions, resistance elements, and other elements which may be needed for proper functioning, all formed by integrated circuit techniques on the suitable substrate, which may be formed from single-crystal silicon.

Another object of the invention is to provide a dew point sensing device that is simple in construction, economical to manufacture, fast in response, and simple and efficient to use.

GENERAL DESCRIPTION OF DRAWINGS

DETAILED DESCRIPTION OF DRAWING

Figure 2:
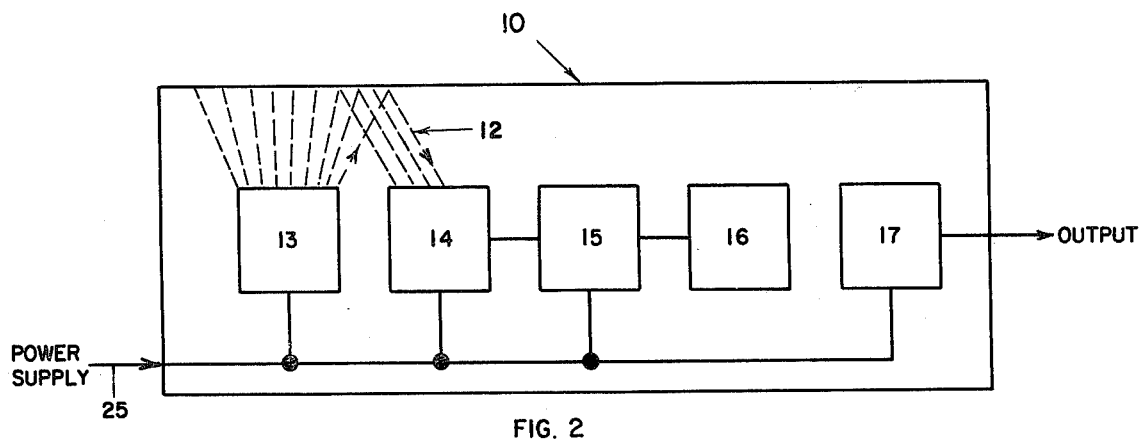
FIG. 2 is a block diagram of the sensing device, according to the invention.
Figure 1:
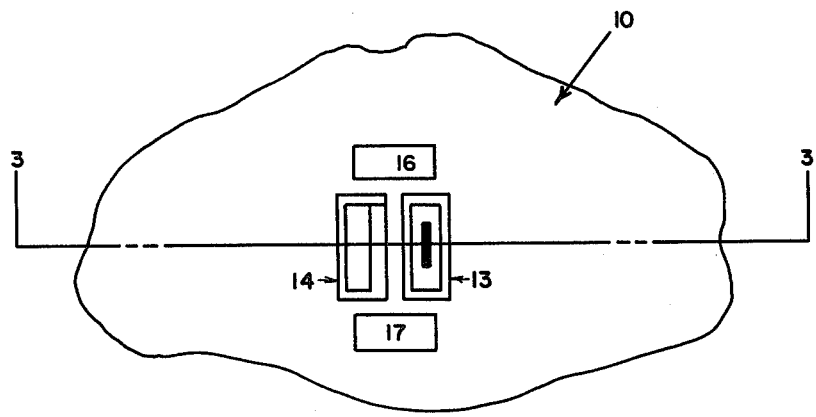
FIG. 1 is a plan view of primary junctions.
Figure 3:
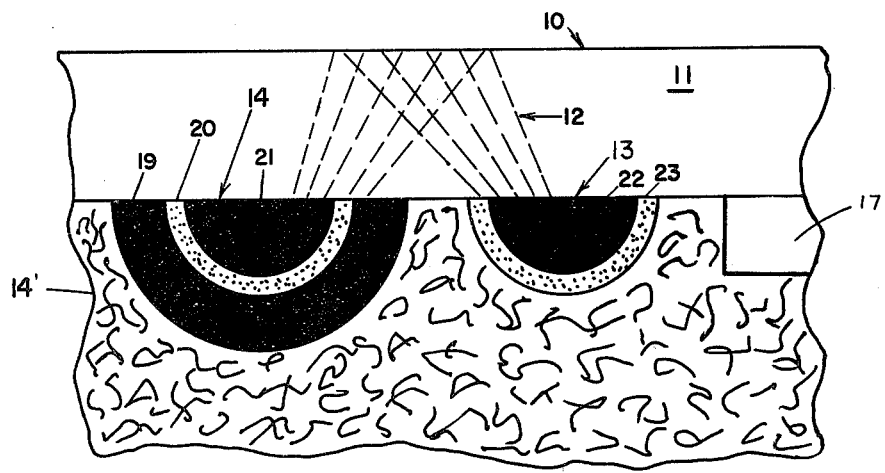
FIG. 3 is a cross-sectional view, taken on line 3—3 of FIG. 2.
Figure 4:
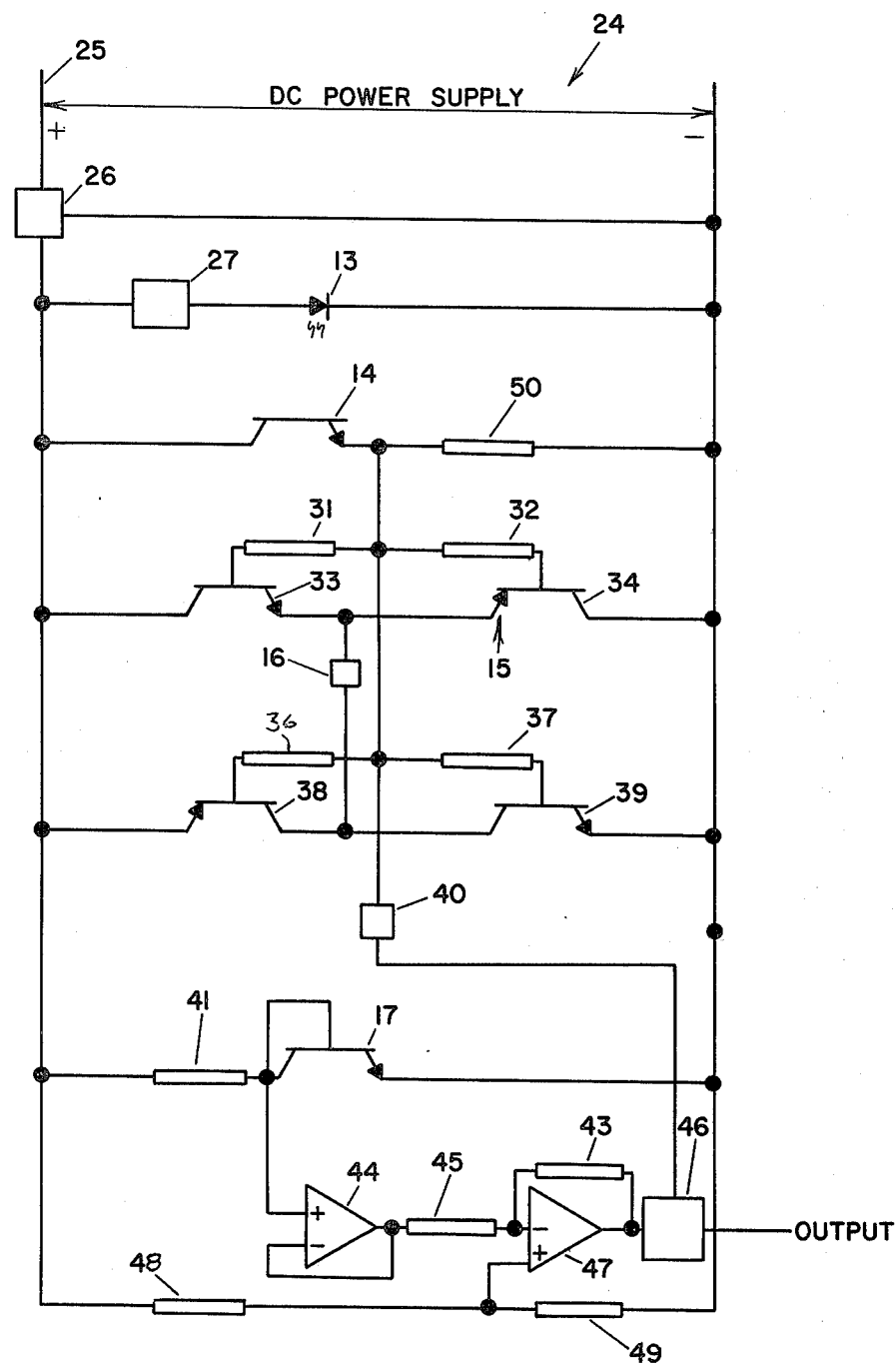
FIG. 4 is schematic diagram of a dew point sensing device according to the invention.

A block diagram, FIG. 1, of the device according to the invention shows generally how the actual circuit may be organized. FIG. 2 shows a plan view of the sensor. FIG. 3 shows a cross-sectional view of the sensor taken on line 13—13 of FIG. 2. In FIG. 3 the sensor is shown made up of the semi-conductor junctions 13, 14, 16 and 17 formed by integrated circuit techniques on a suitable substrate 14' which may be, but is not confined to, single crystal silicon. The insulating layer 11 is supported on the substrate 14' over the junctions. Junction 14 may be a photo transistor having an emitter 19, a base 20 and a collector 21. The LED junction 13 may have a P type silicon 22 and an N type silicon 23, all fabricated as a monolithic, integrated device with insulating layer 11. As shown in FIG. 3, a LED 13 projects light onto the surface 10 which is reflected onto phototransistor junction 14 its intensity determined by the reflectivity of surface 11. Assume that: (A) The insulating layer 11 is at a temperature significantly above the dew point of the ambient gas; (B) The index of refraction, for the light used internally in the sensor, of the surface layer of the sensor is significantly different than the index of the refraction of the surrounding gas, but very close to the index of refraction of the condensed vapor on surface 10.

A voltage regulator 26 supplies constant voltage to the remainder of the circuit. The voltage regulator consists of several semi-conductor junctions and other elements connected in and any of the well-known voltage regulator circuits. A current regulator 27 of a type familiar to those skilled in the art, supplies a constant current to the light source.

Initially, because of the difference in index of refraction, of the sensor, and the surrounding gas, a large portion of the light from light emitting diode 13 is reflected from the surface 10 of the sensor, and thus falls on a phototransistor or other light-sensitive semi-conductor device 14. The resulting current from semiconductor 14 through resistor 50 gives rise to a voltage, which is applied through resistor 31 and 37 to the base of the transistors 33 and 39, causing transistors 33 and 39 to pass current through the Peltier junction 16 causing junction 16 to absorb heat and cool the sensor 17. At the same time, the voltage from transistor 14 and resistor 50 is applied through resistors 36 and 37 to the bases of the PNP transistors 34 and 38, causing 34 and 38 to turn off, thus preventing short circuits.

Resistor 41 supplies current to temperature-sensing device 17, and the base-emitter voltage of 17, which is an indication of temperature of the sensor, is amplified through the circuit consisting of operational amplifiers 44 and 47 with resistors 43, 45, 48 and 49, which is a well-known temperature measuring circuit, having good linearity of output voltage with respect to temperature.

When the sensor reaches the dew point temperature, vapor condenses on the surface 10 of the sensor. When the film of condensed vapor reaches a thickness equal to one-quarter wave length of the light from the light emitting diode 13, the amount of light reflected from the surface back to the interior of the sensor decreases abruptly. This effect is especially strong when the thickness of the layer of condensed vapor is one-fourth wave length of the light from 13.

The decrease in reflected light falling on 14 results in the voltage output of 14 and 50 falling to near zero. This, in turn, shuts off transistors 33 and 34 and turns on transistors 38 and 39, thus reversing the current through the Peltier junction 16 and generating heat to raise the temperature of the insulating layer and sensor 17.

Simultaneously, the sudden decrease in voltage from 14 and 30 is applied to a "one-shot" circuit 40, which generates a brief voltage pulse. This voltage pulse momentarily turns on the input of sample-and-hold circuit 46, so that 46 stores a voltage equal to the output of the temperature measuring circuit until the next dew point measurement is made.

When the temperature of the sensor has risen enough so that the condensed vapor evaporates from the surface 10 of the sensor (which will occur very rapidly, since the layer of condensed vapor is very thin), light will again be reflected internally from the outer layer of the sensor, starting the cooling cycle over again.

Because of the small size and mass of the integrated dew point sensor, the heating/cooling cycle can take place very rapidly, thus permitting almost continuous monitoring of the dew point, as compared to earlier devices.

The foregoing specification sets forth the invention in its preferred, practical forms but the structure shown is capable of modification within a range of equivalents without departing from the invention which is to be understood is broadly novel as is commensurate with the appended claims.

The embodiments of the invention in which an exclusive property or privilege is claimed are defined as follows:

1. A dew point sensor comprising,
    an insulation means having a first side and a second side,
    said first side of said insulation means having a reflecting surface on said first side,
    radiation-emitting means on said sensor on said second side of said insulation means,
    electronic circuit means including radiation sensing means and cooling means and temperature sensing means on the second side of said insulation means,
    output means connected to said circuit means,
    said insulation means being relatively transparent to the radiation emitted by said radiation-emitting means,
    said reflecting surface being adapted to be exposed to a gas containing vapor and adapted to condense said vapor at a temperature at the dew point of said gas,
    said insulation means having a refractive index substantially different from either the gas whose dew point is being measured or the condensed vapor of said gas but not necessarily different than both,
    said insulation means being a relatively good electrical insulator,
    said cooling means being disposed in heat transfer relation with said insulation means whereby when no condensation is formed on said reflecting surface a portion of emitted radiation is refracted and a substantial portion of said radiation from said radiation means is reflected onto said radiation sensing means allowing current to flow through said radiation sensing means and said electronic circuit thereby cooling said insulation means and causing condensation to form on said reflecting surface thereby changing the ratio of reflection at said surface whereby said reflected radiation to said radiation sensing means is decreased and current flow through said circuit is decreased, reversing the cooling effect of said circuit and providing an indication of dew point temperature from said temperature sensing means.

2. The sensor recited in claim 1 wherein the index of refraction of said reflecting surface is very close to the index of refraction of said condensation whereby the light reflected decreases abruptly when said condensation forms on said reflecting layer.

3. The sensor recited in claim 1 wherein a switching means is provided for periodically reversing the flow of current through said heating and cooling means whereby said surface is selectively heated and cooled, thereby providing continuous monitoring of dew point.

4. A dew point sensor comprising a monolithic structure covered by an insulation layer having a first side and a second side,
    a reflecting surface on said first side,
    a Peltier junction,
    a photo transistor junction,
    a light emitting junction,
    a temperature responsive junction,
    said photo transistor junction, said light emitting junction, said photo said Peltier junction,
    and said temperature responsive junction being on said second side,
    said insulation layer being generally transparent to a particular wave length of said light emitting junction,
    an electronic circuit connecting said junctions and supported on a substrate,
    said insulation layer being relatively transparent to the radiation of said light emitting junction, said reflecting surface being adapted to be exposed to a gas containing vapor and adapted to condense said vapor at a temperature at the dew point of said gas,
    said Peltier junction comprising cooling means connected to said photo transistor,
    said Peltier junction being disposed in heat transfer relation with said insulation layer whereby when no condensation is formed on said reflecting surface a portion of said radiation is refracted and a substantial portion of radiation from said light emitting junction is reflected onto said photo transistor allowing current to flow through said photo transistor and said electronic circuit thereby cooling said insulation means and causing condensation to form on said reflecting surface thereby changing the ratio of reflection at said reflecting surface whereby said reflected radiation to said photo transistor is decreased and current flow through said circuit is decreased, reversing the cooling effect of said Peltier junction and providing an indication of dew point temperature from said temperature sensing means,
    means to connect a source of electricity to said circuit in a direction to cause said Peltier junction to absorb heat, whereby said outer surface of said insulating layer is cooled, causing said vapor to condense on said surface thereby changing the reflection of light from said surface,
    whereby the light reaching said photo transistor junction is changed abruptly,
    thereby changing the electrical conduction of said photo transistor.

5. The sensor recited in claim 4 wherein said insulation means is integrated on a substrate.

6. The combination recited in claim 5 wherein said semiconductor substrate is single crystal silicon.

* * * * *